(12) United States Patent
Deinlein et al.

(10) Patent No.: US 11,980,487 B2
(45) Date of Patent: May 14, 2024

(54) COLLISION-FREE X-RAY TUBE MOVEMENT

(71) Applicant: Siemens Healthcare GmbH, Erlangen (DE)

(72) Inventors: Andreas Deinlein, Bayreuth (DE); Matthias Mueller, Bamberg (DE); Rolf Schmidt, Immenreuth (DE); Thomas Dippl, Pressath (DE); Franz Dirauf, Bad Staffelstein (DE); Thorsten Gecks, Weidenberg (DE); Claus-Guenter Schliermann, Kemnath (DE); Franz Fuetterer, Puechersreuth (DE); Thomas Pfeiffer, Adelsdorf (DE); Alexander Beer, Kulmbach (DE); Dieter Heinl, Erbendorf (DE); Wolfgang Neuber, Pressath (DE)

(73) Assignee: Siemens Healthineers AG, Forchheim (DE)

(*) Notice: Subject to any disclaimer, the term of this patent is extended or adjusted under 35 U.S.C. 154(b) by 215 days.

(21) Appl. No.: 17/479,273

(22) Filed: Sep. 20, 2021

(65) Prior Publication Data
US 2022/0096027 A1     Mar. 31, 2022

(30) Foreign Application Priority Data
Sep. 29, 2020  (DE) .................... 10 2020 212 270.9

(51) Int. Cl.
*A61B 6/00*   (2006.01)
*A61B 6/10*   (2006.01)
*G06T 7/50*   (2017.01)

(52) U.S. Cl.
CPC .............. *A61B 6/102* (2013.01); *A61B 6/547* (2013.01); *G06T 7/50* (2017.01); *G06T 2207/10028* (2013.01); *G06T 2207/10116* (2013.01)

(58) Field of Classification Search
CPC ..... A61B 6/102; A61B 6/4464; A61B 6/4476; A61B 6/547
See application file for complete search history.

(56) References Cited

U.S. PATENT DOCUMENTS

2013/0121477 A1* 5/2013 Lee ..................... A61B 6/4482
                                                378/197
2014/0376790 A1* 12/2014 Mostafavi ................ G06T 7/74
                                                382/128
(Continued)

FOREIGN PATENT DOCUMENTS

| DE | 102008046344 A1 | 3/2010 |
| EP | 2916141 A1 | 9/2015 |
| GB | 2564741 A | 1/2019 |

OTHER PUBLICATIONS

Triebel et al; "Multi-Level Surface Maps for Outdoor Terrain Mapping and Loop Closing"; University of Freiburg; 2006; http://ais.informatik.uni-reiburg.de/publications/papers/triebel06iros.pdf.
(Continued)

*Primary Examiner* — Dani Fox
(74) *Attorney, Agent, or Firm* — Harness, Dickey & Pierce, P.L.C.

(57) ABSTRACT

A stand is for a medical imaging system. In an embodiment, the stand includes an X-ray tube; a driver to adjust the X-ray tube in at least three spatial degrees of freedom; at least one environmental sensor to acquire at least one environmental parameter; and a controller to control an adjustment movement of the X-ray tube by generating control signals for the
(Continued)

drive unit and to adapt the adjustment movement based on the at least one environmental parameter.

22 Claims, 8 Drawing Sheets

(56) References Cited

U.S. PATENT DOCUMENTS

| | | |
|---|---|---|
| 2017/0128030 A1 | 5/2017 | Kong et al. |
| 2018/0164419 A1 | 6/2018 | Ärlelid et al. |
| 2021/0038174 A1 | 2/2021 | Beer et al. |

OTHER PUBLICATIONS

German Office Action date May 21, 2021.

* cited by examiner

COLLISION-FREE X-RAY TUBE MOVEMENT

PRIORITY STATEMENT

The present application hereby claims priority under 35 U.S.C. § 119 to German patent application number DE102020212270.9 filed Sep. 29, 2020, the entire contents of which are hereby incorporated herein by reference.

FIELD

Example embodiments of the invention generally relate to a ceiling stand, a medical imaging system and a method for controlling an adjustment movement of an X-ray tube of the imaging system, wherein the control takes into account at least one environmental parameter of the X-ray tube acquired via the sensor unit.

BACKGROUND

To record an X-ray image with a medical imaging system, in particular a radiographic X-ray imaging system, the X-ray tube or the X-ray source must be aligned with the X-ray detector. Herein, first, the X-ray detector is positioned relative to the patient in order to be able to map the body region to be examined. For recordings with a standing patient, this is conventionally done on a bucky wall stand (BWS) by adjusting the height of the X-ray detector. For recordings with a lying patient, a detector bucky arranged in a patient table below the table top is displaced. Then, an X-ray tube ceiling stand (tube stand) on which the X-ray tube is arranged adjustably is aligned in different degrees of freedom (maximum three translational and three rotational axes) so that the X-ray beam emitted by the X-ray tube penetrates the patient at the correct position with the correct angle according to the body region to be examined and completely hits the X-ray detector. The ceiling stand can be positioned manually by an operator (manual operation) or in a motorized manner. In particular when the movement is performed in a motorized manner, there is in principle a risk that the patient, the operator, other people present in the room, or room equipment, for example tables, cupboards, carts, ECG or ultrasound devices, IV stands, wheel chairs or the like could be injured or damaged by a collision with the ceiling stand or the X-ray tube.

Consequently, the operator has to monitor the adjustment movement visually and is responsible for the safe movement of the X-ray tube in the movement area. To ensure this, in addition to a movement actuation button for a specific axis/direction of movement, it is additionally necessary for a release button (dead man's grip, DMG) to be actuated in order to reliably prevent an impending collision by its release.

The operator must therefore continuously ensure that the movement path (trajectory) of the motorized ceiling stand is free in order to be able to move unimpeded from the starting position to the desired target position. For this, the operator must be very familiar with the path curves (trajectories) of the ceiling stand in order to be able to judge where people or objects may be located in the room to avoid their colliding with the ceiling stand when it is moved automatically or in a motorized manner. When the operator releases the release button, movement is halted immediately. Hence, the operator is capable of and responsible for identifying an imminent collision of the ceiling stand with a person and averting it by releasing the release button.

This requires a great deal of time and personnel effort. Therefore, the X-ray tube method represents a major challenge in particular for inexperienced personnel.

To simplify this initial situation, a known method for preventing an undesired collision with immobile fixtures in the treatment room is the use of path planning for a motorized movement of an X-ray tube or other medical units, such as, for example, a robot arm. For this purpose, the room layout has to be configured during the commissioning of the medical imaging system. This means that an installation technician or service technician has to record the room arrangement and geometry once and file it in a control or computing unit of the system. In this way, stationary objects are known to the system and can be taken into account during the automatic path planning. An operator now only has to release the automatic movement by pressing a button, but no longer has to specify the direction of movement or the movement path.

SUMMARY

The inventors have discovered, however, that in the system above, the system does not recognize dynamic obstacles, i.e., a person or mobile fixtures, as such items cannot be rigidly modeled. At least in the case of incorrect operation, this can lead to collision with an obstacle or a person.

In contrast, at least one embodiment of the present invention provides alternative device(s) that allow automatic collision-free and error-free positioning of an X-ray tube in an environment with dynamic obstacles. In particular, at least one embodiment of the present invention reduces or even minimizes the use of personnel and the associated expenditure of time when positioning the X-ray tube.

Embodiments are directed to a stand, a medical imaging system and a method for controlling the same. These and preferred and/or alternative advantageous embodiment variants are the subject matter of the claims.

The following explains the way the embodiments of the invention are achieved with respect to the claimed method and with respect to the claimed apparatus. Features, advantages or alternative embodiments can likewise be transferred to the other claimed subject matter and vice versa. In other words, substantive claims (which are, for example, directed at a method) can also be developed with features described or claimed in connection with the apparatus. Herein, the corresponding functional features of the method are embodied by corresponding substantive modules or units.

In a first embodiment, the present invention relates to a stand for a medical imaging system comprising
 an X-ray tube and
 a drive unit, wherein the stand is embodied to adjust the X-ray tube via the drive unit in at least two spatial degrees of freedom,
 a sensor unit comprising at least one environmental sensor embodied to acquire at least one environmental parameter, and
 a control unit embodied to control an adjustment movement of the X-ray tube by generating control signals for the drive unit and to adapt the adjustment movement based on the at least one environmental parameter.

A further embodiment of the present invention relates to a medical imaging system, for example comprising a stand according to at least one embodiment of the invention. The medical imaging system of at least one embodiment is used to acquire medical image data for a patient. The medical imaging system further comprises an X-ray detector embodied to detect the X-rays generated and emitted by the X-ray tube, which have been attenuated by the patient. In preferred embodiments, the X-ray detector is embodied as a digital flat panel detector. The medical imaging system is preferably embodied as a radiography system. The medical imaging system further also comprises a computing unit for controlling the image recording process and/or for (further) processing the acquired image data. In preferred embodiments, the control unit is embodied as a module of the system computing unit. Advantageously, the control unit is thus integrated in the medical imaging system. Alternatively, the control unit can also be embodied separately and in particular embodied on the stand itself. The control unit can alternatively also be embodied centrally and can in particular process sensor signals and/or adapt the adjustment movement for one stand or for a plurality of stands of a plurality of medical imaging systems in parallel, for example in a radiology center or hospital comprising a plurality of imaging systems.

In a further embodiment, the present invention relates to a method for controlling a stand according to the invention. The method comprises:

acquiring at least one spatial environmental parameter via the sensor unit; and controlling an adjustment movement of an X-ray tube via the control unit, wherein the controlling comprises generating control signals for a drive unit and adapting these based on the at least one environmental parameter.

In a further embodiment, the present invention relates to a stand for a medical imaging system, comprising:

an X-ray tube; and a driver, to adjust the X-ray tube in at least two spatial degrees of freedom;

at least one environmental sensor to acquire at least one environmental parameter; and a controller to control an adjustment movement of the X-ray tube by generating control signals for the driver and to adapt the adjustment movement based on the at least one environmental parameter.

In a further embodiment, the present invention relates to a method for controlling a stand for a medical imaging system, the stand including an X-ray tube, a driver to adjust the X-ray tube, at least one environmental sensor, and a controller, the method comprising:

acquiring at least one spatial environmental parameter via the at least one environmental sensor;

controlling an adjustment movement of an X-ray tube via the controller, the controlling including generating control signals for the driver and adapting the control signal based on the at least one environmental parameter.

BRIEF DESCRIPTION OF THE DRAWINGS

The above-described properties, features and advantages of this invention and the manner in which these are achieved will become clearer and more plainly comprehensible in conjunction with the following description of the example embodiments explained in more detail in conjunction with the drawings. This description does not restrict the invention to these example embodiments. In different figures, the same components are given identical reference characters. The figures are generally not true to scale. The figures show.

DETAILED DESCRIPTION OF THE EXAMPLE EMBODIMENTS

Figure 1:
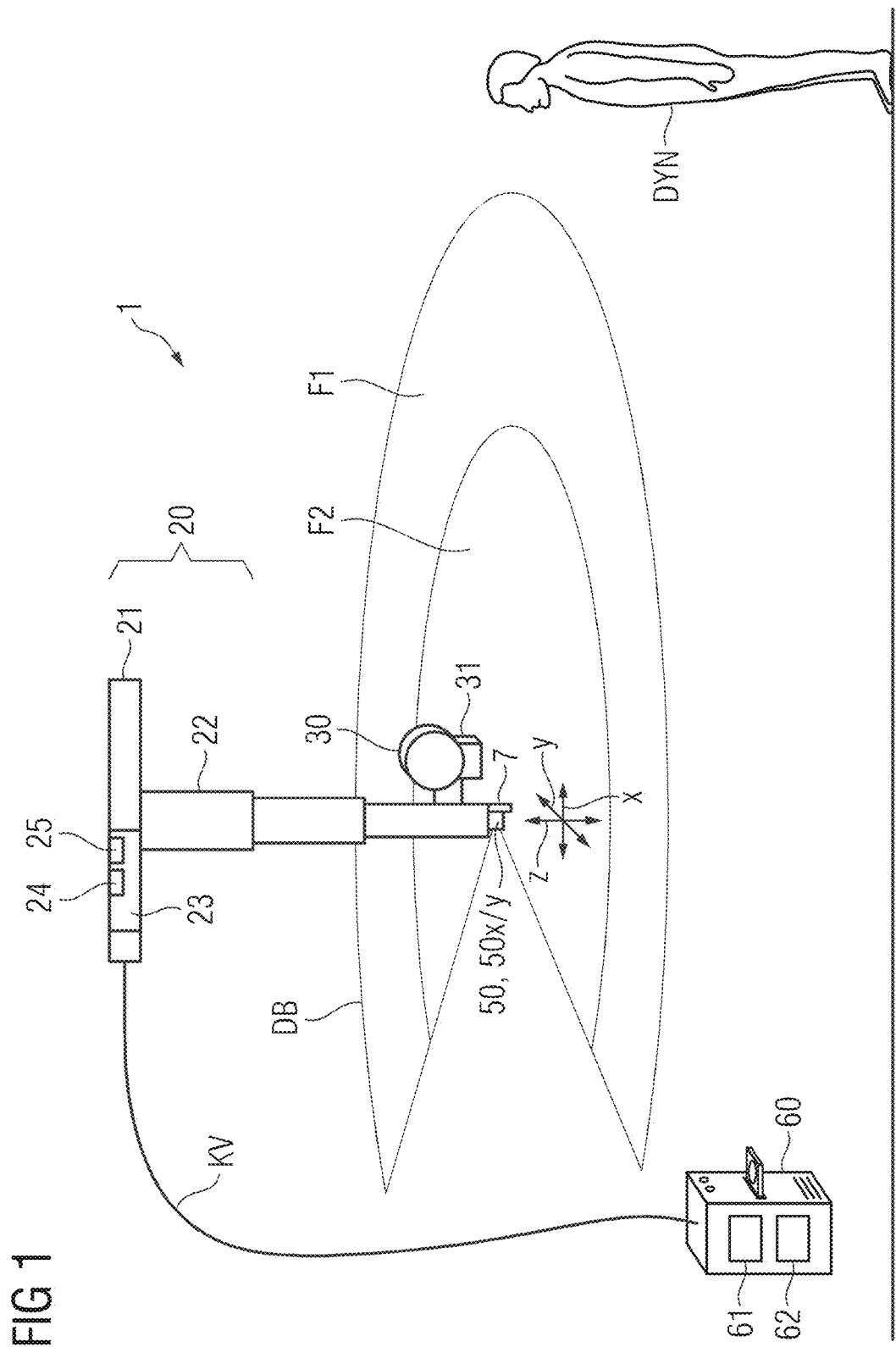
FIG. 1 a view of a medical imaging system according to the invention in the form of an X-ray imaging system together with a stand according to an embodiment of the present invention, FIG. 2 an expanded view of the medical imaging system according to an embodiment of the invention according to FIG. 1, FIG. 3 a detailed view of a medical imaging system according to the invention according to an alternative embodiment, FIG. 4 a detailed view of a stand according to an embodiment of the invention for a medical imaging system according to a combination of FIGS. 1 and 2, FIG. 5 a view of a medical imaging system in another embodiment, FIG. 6 a detailed view of a stand according to an embodiment of the invention for a medical imaging system according to FIG. 5, and FIG. 7 a view of a medical imaging system in a further embodiment, and FIG. 8 a method for controlling a stand in an embodiment of the present invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In a first embodiment, the present invention relates to a stand for a medical imaging system comprising
an X-ray tube and
a drive unit, wherein the stand is embodied to adjust the X-ray tube via the drive unit in at least two spatial degrees of freedom,
a sensor unit comprising at least one environmental sensor embodied to acquire at least one environmental parameter, and
a control unit embodied to control an adjustment movement of the X-ray tube by generating control signals for the drive unit and to adapt the adjustment movement based on the at least one environmental parameter.

The stand realizes a space-saving and movable support for an X-ray tube. The stand can be embodied as a floor stand or as a ceiling stand.

In embodiments with a floor stand, the X-ray tube is attached to the floor of an examination room by the floor stand. The floor stand can be embodied as fixed in one position or as mobile and can be positioned anywhere in the room. In some embodiments, the floor stand can comprise a lifting device embodied to adjust the X-ray tube in the vertical direction in the sense of a height adjustment. For example, the floor stand has a vertical guide rail on which the X-ray tube is arranged in a height-adjustable manner or a telescopic arm. In addition, the floor stand can have a rotation module with which the X-ray tube can be rotated about at least one axis of rotation and at most three axes of rotation.

In other embodiments, the X-ray tube is attached to the ceiling of an examination room by the ceiling stand. In some embodiments, the ceiling stand can comprise a horizontal module in order to enable a horizontal movement of the X-ray tube. The horizontal module can, for example, be realized by guide rails and/or a carriage. The ceiling stand can further comprise a lifting device embodied to adjust the X-ray tube in the vertical direction in the sense of a height adjustment. The lifting module is preferably embodied as a telescopic arm, which can be retracted in a particularly space-saving manner, at the lower end of which the X-ray tube is mounted. In addition, the ceiling stand can have a rotation module with which the X-ray tube can be rotated about at least one axis of rotation and at most three axes of rotation. In some embodiments, the ceiling stand has the following motorized axes:

longitudinal—linear movement in the x direction
transversal—linear movement in the y direction
lift—linear movement in the z direction
RVA—rotation about the vertical (z) axis
RHA—rotation about the horizontal (x/y) axis The drive unit of the stand, in at least one embodiment, acts on the mobile components of the stand, such as guide rail, carriage, telescopic arm, rotation module, etc. and is embodied to drive or adjust them in accordance with (partially) autonomous operation. Herein, the drive unit can comprise different drive modules for the vertical module, the lifting module and/or the rotation module. The drive unit or at least one of the modules thereof advantageously comprises a motor, preferably an electric motor. In particular, the electric motor is embodied as an electromechanical converter.

The stand, in at least one embodiment, is further characterized by a sensor unit comprising at least one environmental sensor embodied to acquire at least one environmental parameter. Consequently, the sensor unit is embodied to acquire an environmental parameter characterizing or describing the environment of the stand in particular the environment of the X-ray tube. In particular, the sensor unit is embodied to acquire the environmental parameter continuously and in particular during an adjustment movement of the X-ray tube. Particularly preferably, the sensor unit acquires a plurality of environmental parameters simultaneously.

The environmental parameter comprises at least one indication, information, a measured value indicating whether an object, an obstacle, a person, in particular a dynamic obstacle that moves freely in the room is located in the immediate vicinity of the X-ray tube.

The stand, in at least one embodiment, further comprises a control unit. This can be embodied as a computing unit or computer. The control unit according to the invention basically controls an adjustment movement of the X-ray tube by generating control signals for the drive unit, for example based on a previously filed or defined map of the environment, user commands received via an operator interface and/or a specified target position for the X-ray tube. According to the invention, the control unit is embodied to adapt the control signals for the or the adjustment movement based on the at least one environmental parameter. In other words, the control unit comprises control logic or a computing rule which takes the at least one environmental parameter into account and ascertains a movement trajectory dependent thereon and/or a changed target position and generates and sends corresponding control signals for the drive unit.

The inventors, in at least one embodiment, have recognized that the provision of a sensor unit on the stand and a control unit that takes sensor signals into account can ensure the necessary collision protection for the operator. This enables the motorized movements of the stand or the X-ray tube to be executed without the permanent active consent of the operator.

A further embodiment of the present invention relates to a medical imaging system, for example comprising a stand according to at least one embodiment of the invention. The medical imaging system is used to acquire medical image data for a patient. The medical imaging system further comprises an X-ray detector embodied to detect the X-rays generated and emitted by the X-ray tube, which have been attenuated by the patient. In preferred embodiments, the X-ray detector is embodied as a digital flat panel detector. The medical imaging system is preferably embodied as a radiography system. The medical imaging system further also comprises a computing unit for controlling the image recording process and/or for (further) processing the acquired image data. In preferred embodiments, the control unit is embodied as a module of the system computing unit. Advantageously, the control unit is thus integrated in the medical imaging system. Alternatively, the control unit can also be embodied separately and in particular embodied on the stand itself. The control unit can alternatively also be embodied centrally and can in particular process sensor signals and/or adapt the adjustment movement for one stand or for a plurality of stands of a plurality of medical imaging systems in parallel, for example in a radiology center or hospital comprising a plurality of imaging systems.

The control unit advantageously comprises an interface configured to acquire or receive a sensor signal in the form of the at least one environmental parameter and a calculating unit for calculating or generating control signals adapted thereto. The computing unit preferably comprises an interface configured to output the control signals to the drive unit. The receiving interface can be embodied as an assembly that is separate from the output interface. However, both interfaces can also be combined in one interface assembly. Particularly preferably, the interfaces of the control unit are embodied for optical data communication.

In one embodiment of the invention, the sensor unit comprises a plurality of environmental sensors. A plurality of, i.e., at least two, environmental sensors are particularly well suited for monitoring the environment of the X-ray tube, preferably completely, and thus for avoiding undesired collisions as effectively as possible. As an alternative to this, it is also possible for only one environmental sensor to be comprised. This is then preferably embodied with a particularly large field of view or detection field. If a plurality of environmental sensors are provided, accordingly a plurality of environmental parameters are acquired and transmitted to the control unit.

According to an embodiment of the invention, the environmental sensors are not restricted to a specific technology. An environmental sensor can preferably be embodied as an optical or acoustic sensor. An environmental sensor can, for example, be embodied as a multi-technology radar sensor, a laser scanner, a LiDar (light detection and ranging) system, a ToF (time of flight) system, as an ultrasound sensor, as a three-dimensional camera or the like. Mixed forms of environmental sensors can be provided in the sensor unit as can a plurality of identical environmental sensors.

In a further preferred embodiment, the sensor unit is embodied to acquire an environmental parameter in the form of a distance or a distance profile depending on the embodiment of the at least one environmental sensor. Herein, the distance relates to the distance between an object, an obstacle, a person or the like comprising a dynamic obstacle and the environmental sensor or the X-ray tube. A relative position between the environmental sensor and the X-ray tube can be determined in advance and filed so it can be retrieved for the control unit. Herein, a distance profile describes a plurality of spatially encoded distance values, which, depending on the size of the detection range of the environmental sensor, can be limited to an object, an obstacle or a person, in particular a dynamic obstacle or, however, can also include all surrounding objects in the environment. In this embodiment, the at least one environmental parameter advantageously provides the control unit with an environmental profile based on which an adjustment movement of the X-ray tube can be determined or adapted.

In a further embodiment of the invention, at least one environmental sensor is arranged on the X-ray tube with a horizontally aligned detection field. Herein, the detection field of the environmental sensor does not have to be limited to the horizontal plane. In this way, at least the horizontal plane (x/y plane) around the X-ray tube is monitored. Herein, the environmental sensor can, for example, be arranged in the housing of the X-ray tube. Alternatively, it can be built into the collimator the X-ray detector. In other embodiments, the environmental sensor is only arranged at the height of the X-ray tube, for example also at the lower end of the telescopic arm of a stand embodied as a ceiling stand. Alternatively, however, the environmental sensor can also be arranged, in particular movably, on a wall of the room, and track a change in the height of the X-ray tube via the telescopic arm, for example via a rail system on the wall of the room.

In one embodiment of the invention, an environmental sensor can, for example, be provided in the form of a two-dimensional laser scanner. In the case of a ceiling stand, this can be attached in the lower region of the ceiling stand, i.e. at the height of the X-ray tube. This permanently scans the room surrounding the X-ray tube in a horizontal direction in order to identify an impending collision with a person (or an object). The laser scanner continuously supplies distance values for objects located in the vicinity of the X-ray tube as environmental parameters.

The at least one environmental sensor is preferably embodied as a safe environmental sensor, for example as a safe radar sensor or ultrasound sensor. A safe laser scanner covers, for example in the horizontal plane, an angular range of 270°, in other words, the detection range of a safe laser sensor covers this angular range. If only one laser scanner is used, it can be provided according to the invention that a movement of the stand corresponding to the adjustment movement of the X-ray tube is kept within the detection range of the laser scanner. In this way, collisions can be reliably avoided. Alternatively, to expand the detection range of the environmental sensor, it can be provided that the laser scanner itself is rotated about its vertical axis (z axis) and the detection range adjusted thereby. This enables an adjustment movement for the X-ray tube in all spatial directions. In another alternative, a second laser scanner can be provided at substantially the same position with its detection field rotated by 180° about its vertical axis relative to the detection field of the first laser scanner. This enables simultaneous 360° monitoring in the horizontal plane.

The described laser scanners enable safeguarding of adjustment movements of the X-ray tube at least in the horizontal plane (x/y plane). For a vertical adjustment movement (z direction), the sensor unit can additionally comprise at least one tactile sensor arranged, for example, below the laser scanner and/or the X-ray tube, which generates a corresponding sensor signal upon contact with an object. In this way, at least in the z direction, collision monitoring can be realized that, for example, halts the movement of the X-ray tube. The tactile sensor can, for example, be embodied as an electro-mechanical sensor, as a capacitive or electro-magnetic sensor.

In a further particularly preferred embodiment, at least one environmental sensor of the sensor unit is embodied as a three-dimensional sensor. As an alternative to this, a plurality of environmental sensors with smaller dimensions can be combined in order to achieve three-dimensionality. Three-dimensional environmental sensors or a three-dimensional overall detection field have the advantage that they cover the entire movement space relevant for an adjustment movement of the X-ray tube in all three spatial directions 'at a glance', i.e. at the same time and can supply environmental parameters therefor, for example in the form of depth information.

A particularly preferred three-dimensional environmental sensor is a three-dimensional optical camera. As an alternative to this, it is possible to use a laser scanner with a laser beam that does not scan a plane or the horizontal plane as described above but traverses the lateral surface of a cone during the scanning movement. This can, for example, be realized with a mirror arrangement with an adjustable exit angle. Thus, in deviation from a 90° angle, the laser beam can, for example, exit at an angle of 135°. In this way, the scanning or detection range extends in the z direction. This advantageously enables the acquisition of dynamic objects with a certain minimum extension that (also) move in the z direction.

In a further alternative embodiment, a laser scanner is arranged below the X-ray tube with a detection field aligned downward toward the floor, wherein now the detection field is embodied as rotatable about a horizontal axis. The horizontal axis is preferably, but not necessarily, located in or parallel to the detection field. The horizontal axis can run through the laser scanner itself or through the X-ray tube. In this embodiment, the angular position of the horizontal axis must be unambiguously known, since together with the angular range enclosed by the detection field, this excludes certain directions of movement for the X-ray tube. The rotation about the horizontal axis can, for example, take place via an auxiliary drive which causes an oscillating movement about the horizontal axis. This advantageously enables a particularly high scanning rate for the entire detection range and is independent of an angular position of the X-ray tube. Alternatively, the detector can rotate about the horizontal axis together with the X-ray tube.

In a further alternative, in addition to the above-described laser scanner with a detection range in the horizontal plane, a further laser scanner with a detection range tilted by 90° is provided, for example below the X-ray tube. This ensures collision-free movement of the X-ray tube in the x, y or z direction.

In a further particularly preferred embodiment, instead of a plurality of laser scanners, it is possible to use a multi-plane or 3D laser scanner which monitors a complete volume of space (for example a hemisphere enclosing the X-ray tube). This would also enable an adjustment movement of the X-ray tube in the x, y and z direction and without having to rotate or move the laser scanner. In particular, the embodiment of the invention via a 3D camera corresponds to a cost-effective realization.

Optionally, in all embodiments, the sensor unit can comprise a tactile sensor for collision monitoring, as described above.

In another embodiment, at least one environmental sensor is arranged on a carriage of a stand embodied as a ceiling stand with a vertically downward aligned detection field. In this embodiment, particularly advantageously, at least the immediate environment of the X-ray tube is monitored. Objects that approach the X-ray tube within the detection range of the environmental parameter are thus reliably acquired. The environmental sensor preferably detects, preferably continuously, at least one distance value so that an adjustment movement can be adapted thereto by the control unit.

In one embodiment, one or more environmental sensors in the form of depth sensors, for example 3D cameras, can be positioned on the carriage, wherein the detection range is in each case aligned downward toward the floor. The sensor/sensors are thus moved along with the movement of the carriage and therefore always cover the region around the X-ray tube. Preferably, the entire detection range around the X-ray tube is completely enclosed. The number of environmental sensors and the precise attachment can be optimized such that the entire detection range formed by the individual detection ranges around the telescopic arm or the X-ray tube is as large as possible. The 3D camera or cameras preferably provide a height profile for the environment comprising all further objects for the X-ray tube as environmental parameters.

In alternative embodiments, the at least one environmental sensor can also be arranged in the upper region of the ceiling stand close to the ceiling of the room. It does not move with the movement of the carriage. This is in particular possible with detection ranges of the environmental sensors that are large per se so that the environment thereof is monitored independently of the position of the X-ray tube. Alternatively, the environmental sensor can be arranged on its own carriage and thus track the movement of the X-ray tube.

In one particularly preferred embodiment, the X-ray tube is located in the detection field of at least one environmental sensor.

In other words, in this embodiment, the X-ray tube itself is acquired as a detected object by the environmental sensor. For example, the environmental sensor can generate a distance profile comprising distance values to the X-ray tube as environmental parameters. In this way, the relative position between the environmental sensor and the X-ray tube, but also between the X-ray tube and the object or person is known directly from the distance profile as a separate environmental parameter. On the one hand, this ensures that the environmental sensor always reliably monitors the environment of the X-ray tube. On the other hand, this embodiment also enables simplified calibration of the medical imaging system on commissioning, since the relative position of the X-ray sensor and the environmental sensor no longer needs to be determined in advance. In addition, error or service diagnostics with respect to the position of the X-ray tube can be simplified.

In a further embodiment of the invention with a plurality of environmental sensors, the detection ranges of at least two environmental sensors at least partially overlap.

In another embodiment, the environmental sensors can be arranged such that their detection fields form an envelope curve around the X-ray tube.

Here, the environmental sensors are preferably arranged in, on or near to the X-ray tube itself, for example within the covering of the collimator. This advantageously enables the entire movement space or the immediate environment of the X-ray tube to be monitored.

Depending on the size of a detection range of an individual environmental sensor, to achieve a completely enclosed entire detection range, a plurality of environmental sensors can be arranged such that their detection ranges adjoin one another. In this way, monitoring of the complete movement space of the X-ray tube is achieved.

The environmental sensors are particularly preferably placed relative to one another such that their individual detection ranges overlap. In this way, at least for the overlapping regions, first-failure safety typical of medical applications is achieved. The overlapping regions are monitored by at least two sensors; therefore, a collision object would be identified by at least one of the two sensors. If one of the two environmental sensors is defective, the overlapping region would still be monitored by the other sensor. For firstfailure-safe identification of collision-free space, the requirement is that a confirmation signal is sent by two sensors.

To achieve first-failure safety for the entire movement space of the X-ray tube, the environmental sensors can be provided completely in redundant form due to the typically low installation space requirement. As an alternative to this, it is possible for only the readout electronics of the environmental sensors to be comprised in redundant form in order to obtain a completely enclosed envelope curve around the X-ray tube in redundant form.

In a further embodiment, the present invention relates to a method for controlling a stand according to the invention. The method comprises:

acquiring at least one spatial environmental parameter via the sensor unit; and controlling an adjustment movement of an X-ray tube via the control unit, wherein the controlling comprises generating control signals for a drive unit and adapting these based on the at least one environmental parameter.

In a further embodiment of the invention, the controlling comprises identifying at least one dynamic obstacle on the basis of the at least one environmental parameter acquired. The dynamic obstacle is an object, an item or a person, that is either moved or is not stationary in the sense that it can be adjusted between different positions on which it can remain at least temporarily. For this purpose, the controlling can comprise comparing distance profiles acquired as environmental parameters at at least two successive points in time with one another. Objects in the environment considered therein, which have a position change, are identified as dynamic objects. In addition, the speed of movement can be derived from the value for the change in position and the time intervals of the distance profiles compared. Alternatively or additionally, a comparison can be made between a current distance profile and a retrievable map of the room for the control unit filed during the commissioning of the medical imaging system comprising all fixed objects in the room, such as examination fixtures or the like, in order to identify objects that were not present during this process as dynamic objects.

A distance profile can preferably be embodied in the form of a depth image of a 3D camera, the detection range of which is aligned downward toward the floor. However, the distance profile is not restricted to embodiments with a horizontal alignment. Rather, a distance profile can also be created in a horizontal direction depending on the alignment of the detection field of the environmental sensor. In preferred embodiments, the distance profile can also be calculated from the sensor signals from different environmental sensors. Similarly, a distance value is also independent of a particular spatial direction, in other words an individual distance value can extend in any spatial direction.

In a further embodiment, the controlling comprises determining a trajectory, speed of movement, direction of movement and/or halting of movement for the X-ray tube that is adapted to the identified dynamic obstacle.

Thus, the adaptation of the control signals based on the environmental parameter can comprise adapting the direction of the adjustment movement, changing speed during the adjustment movement, halting the adjustment movement (at least temporarily) and/or changing a target position. For example, the adaptation can comprise comparing the acquired distance value with a collision object with at least one threshold value corresponding to different safety ranges around the environmental sensor or the X-ray tube. If the value falls below the at least one threshold value, the adjustment movement can, for example, be retarded or halted. In further embodiments, an adaptation of the speed of movement and/or a halting of the adjustment movement may depend on the speed at which the dynamic object is moving.

In one embodiment of the invention, the acquisition of the environmental parameter comprises acquiring a distance profile and the controlling comprises ascertaining a cell-based two-dimensional height map from the distance profile.

In this embodiment, the controlling of the adjustment movement comprises, for example, ascertaining a cell-based two-dimensional height map from a distance profile of the environmental sensor. Herein, a cell covers, for example, a floor area required for a precise movement control, for example an area between 1×1 cm to 10×10 cm. For each cell, a depth value is determined which corresponds to the distance between the object detected in the cell, for example floor, patient table, collision object, etc., and the height of the environmental sensor. The depth value for each cell is maximum if no object is present between the environmental sensor and the floor. The control unit can use this two-dimensional height map as the basis for ascertaining dynamic collision cuboids which are included in the calculation of the path trajectory for the adjustment movement in order to be able to move in a free path from the starting position to the target position despite the presence of dynamic obstacles. Herein, advantageously, the number of dynamic collision cuboids can be optimized, for example by combining adjacent cells with a small height difference to form a common cuboid, wherein the cuboid is assigned the lowest of the depth values comprised. The two-dimensional height map can now be used to plan the path. For example, then advantageously only one height value is applied for the movement for the region occupied by the collision cuboid instead of planning a height value for each of the individual cells.

In a further embodiment, the acquisition of the environmental parameter comprises acquiring a distance profile and the controlling comprises ascertaining a multi-level surface map (MLS) from the distance profile.

In this embodiment, the two-dimensional height map can be supplemented by a multi-level surface map in which a plurality of height levels or distance values are permitted for each cell. This in particular also enables objects, in particular collision objects, directly below the ceiling stand to be taken into account in the map and, if necessary, collision cuboids to be created for them and taken into account in the path planning.

In summary, at least one embodiment of the present invention allows an efficient and robust automatic positioning or adjustment movement of the X-ray tube despite dynamic obstacles, in particular people in the room. At least one embodiment of the invention realizes sensor-based automatic real time monitoring of the room before or while components of the medical imaging system are moving, hence real-time collision identification in the room, and enables real-time adaptation of the adjustment movement. This increases operational safety and reduces the personnel effort required for monitoring during the positioning of the X-ray tube. An operator is no longer necessary during the adjustment movement of the X-ray tube. There is no need to operate the dead man's switch and so the automation of the imaging system is supported.

Automatic error diagnosis for the environmental sensors, which can in particular advantageously take place in the form of online or remote diagnosis, results from a special attachment of environmental sensors in the form of depth sensors. In particular in the case of ceiling stands, these advantageously also map the lower part of the ceiling stand together with the X-ray tube. Since the Z position/height of the X-ray tube is known to the control unit of the ceiling stand or the computing unit of the medical imaging system via additional position sensors in motorized axes of the imaging system, for example the ceiling stand, this can be used for online diagnosis. Moreover, the other objects acquired via depth sensors, in particular further components of the imaging system, such as the patient table or bucky wall stand, can be used for diagnosis since their position is known a priori in each case. In this case, it is ascertained whether the distance profile at the respective positions of the different objects provides the correct height value.

If the at least one environmental sensor is suitably selected and attached, automatic sensor calibration can take place during commissioning/installation of the medical imaging system via position analysis of the X-ray tube and known objects. In this case, a plurality of specifiable positions of the X-ray tube in the x/y/z direction are approached and thus the environmental sensor is calibrated by using further objects taken into account in the distance profile with positions that are known per se as a reference. Moreover, the examination room can be scanned for static obstacles (such as cabinets) on installation and these can be incorporated into a room map with all static obstacles. This minimizes the installation times and increases the robustness of the system. Alternatively, room configuration during commissioning, i.e., the creation of an initial room map for the control unit, can be completely omitted since the imaging system or the stand orients itself in the room independently using the environmental sensors and identifies potential collision objects, in particular dynamic obstacles, during an adjustment movement.

At least one embodiment of the invention also enables distance control to be realized between the X-ray tube and the X-ray detector (SID control). This prevents operating errors or the recording of unusable X-ray images and avoids unnecessary radiation exposure for a patient by reducing the repetition rate of the image acquisition.

In addition, at least one embodiment of the invention also enables position measurement and acquisition in the device axes so that it is possible to dispense with a further redundant measuring sensor mechanism on the device axes that is only provided for this purpose.

FIG. 1 shows a view of a medical imaging system 1 according to an embodiment of the invention in the form of an X-ray imaging system together with a stand 20 in the form of a ceiling stand according to an embodiment of the present invention. The medical imaging system 1 is arranged in an examination room of a medical facility, for example a hospital. The ceiling stand 20 according to an embodiment of the invention comprises a ceiling-mounted rail system 21 by which a carriage (not shown) can be adjusted in the x or y direction below the ceiling of the room. A telescopic arm 22 that can be retracted and extended via an integrated further rail system is arranged on the carriage. An X-ray tube 30 together with a collimator 31 is arranged on a lower, preferably the lowest, telescopic section of the telescopic arm 22. The telescopic arm 22 is embodied to adjust the X-ray tube in the z direction, i.e. to adjust its height. The X-ray tube 30 is further mounted on the telescopic section such that it can be rotated about the z axis together with or independently of the telescopic section. In addition, at least one horizontally extending axis of rotation is provided through the X-ray tube 30 or at least at the height of the X-ray tube 30 about which the X-ray tube 30 can be inclined or tilted. The provision of a plurality of different degrees of freedom, enables the X-ray tube 30 to be brought to the best possible position required for image data acquisition.

The ceiling stand 20 also comprises a drive unit 23 for adjusting the X-ray tube 30 in at least three spatial degrees of freedom. This is embodied to adjust the different movable components of the ceiling stand 22 or the X-ray tube in the different degrees of freedom. For this purpose, the drive unit 23 comprises at least one drive module 25 comprising, for example, an electric motor, a brake and a transmitter, wherein the drive module acts on at least one of the movable components via a mechanical coupling that is known per se, and a drive regulator 24, possibly comprising a movement control regulator (for example STO (safe torque off), SDI (safe direction), SLS (safety limited speed). The drive unit 23 preferably comprises a plurality of drive module-drive regulation pairs, namely one for each degree of freedom provided in the imaging system 1.

The stand 20 embodied as a ceiling stand further comprises a sensor unit 50 comprising an environmental sensor 50$x/y$, here in the form of a laser scanner embodied to acquire at least one environmental parameter. Here, the laser scanner 50$x/y$ is arranged at the lower end of the lowest telescopic section. It is configured to scan the environment of the X-ray tube 30 within a detection range DB for further objects, in particular dynamic obstacles, here illustrated by a person DYN.

In this embodiment, the detection range DB of the laser scanner 50$x/y$ includes an area in the horizontal plane over an angular range of approximately 270°. Therefore, it does not allow monitoring in the z direction or the remaining 90° of the horizontal plane. As an alternative to this, the laser scanner 50$x/y$ can also be arranged directly on the X-ray tube 30 and with a horizontally aligned detection field.

The sensor unit 50 continuously supplies direction-dependent distance data or speeds of movement relating to objects within the detection range DB as environmental parameters. The sensor unit 50 preferably supplies individual distance values and/or a distance profile over its detection range DB as environmental parameters. This in particular enables the ceiling stand 20 to identify dynamic obstacles DYN moving in the room.

In this example, the sensor unit also comprises a tactile sensor 7 for acquiring a collision when the ceiling stand moves in the z direction.

The ceiling stand 20 further comprises a control unit 62, which is here embodied as a submodule of the computing unit 60 of the medical imaging system 1. The control unit 62 is embodied to control an adjustment movement of the X-ray tube 30 by generating control signals for the drive unit 23 and to adapt the adjustment movement based on the at least one environmental parameter. In other words, the control unit 62 is embodied to adapt a movement path and/or a speed of movement of the X-ray tube 30.

Therefore, the control unit 62 processes the acquired sensor signals in the form of environmental parameters and ascertains therefrom a (changed) movement trajectory for the X-ray tube 30. The movement trajectory characterizes a route for the X-ray tube 30 between a starting position, which may correspond to its current position, and an end position. The control unit 62 is further embodied to generate control signals for the drive unit 23.

The computing unit 60 advantageously comprises an interface 61 configured to acquire or receive the at least one environmental parameter. The interface 61 is also used to transmit the control signals to the drive unit 23 via a communication link KV. The interface 61 and the control unit 62 also have a data link to one another. The interface 61 can comprise an input interface and an output interface which can also be embodied separately from one another. However, the two sub-interfaces can also be combined in one interface assembly.

The interface 61 is, for example, realized via a hardware interface or software interface such as a PCI bus, USB or Firewire. Data is preferably exchanged via a network connection. The network can be embodied as a local area network (LAN), for example an intranet or a wide area network (WAN). According to the invention, the network connection is embodied as wireless, for example as a wireless LAN (WLAN or WiFi). The network can comprise a combination of different examples of networks. Data transmission can take place based on a data query or can be self-initiated. Data transmission between two units or system components can be bidirectional or unidirectional.

Advantageously, the computing unit 60 can be arranged in a bucky wall stand (not shown here), in the patient table or on the ceiling stand 20 itself. Alternatively, the control unit 62 can also be embodied as separate from the computing unit 60 of the medical imaging system 1 and arranged separately therefrom. Alternatively, both the computing unit 60 and the control unit 62 can be arranged remotely or apart from the ceiling stand 20 or the medical imaging system 1, for example as part of a central computing and control unit of a medical facility such as a hospital. Data is then advantageously exchanged wirelessly.

The computing unit 60 and/or the control unit 62 can be embodied in the form of hardware or in the form of software. For example, the control unit 62 is embodied as a so-called FPGA (field programmable gate array) or comprises an arithmetic logic unit. The control unit 62 can also be embodied as a (standalone) cloud-based computer, wherein data exchange with the environmental sensor 50 or the drive unit 23 and possibly further components takes place via a secure internet connection.

In this embodiment, the detection range DB is divided into two sub-regions. A warning field F1 extends around the environmental sensor 50 and has a minimum distance to the environmental sensor 50, for example 0.5 m, 1 m or 1.5 m. It covers an outer region of the detection range DB. A protective field F2 has a maximum distance value to the environmental sensor 50*x/y* corresponding to the minimum distance of the warning field F1 and hence covers an internal region of the detection range DB. In this embodiment, the control unit 62 is embodied to compare a distance value, embodied as an environmental parameter, of a dynamic obstacle located in the detection range, in particular a person, with the value for the minimum distance. When the obstacle is identified within the warning field F1, the control unit 62 generates a control signal corresponding to a reduced speed of movement for the X-ray tube 30. When the obstacle is identified within the protective field F2, the control unit 62 generates a control signal corresponding to a halting of the movement. In this way, the adjustment movement of the X-ray tube is safely halted. A collision can be completely ruled out by the protective measures mentioned.

Figure 2:
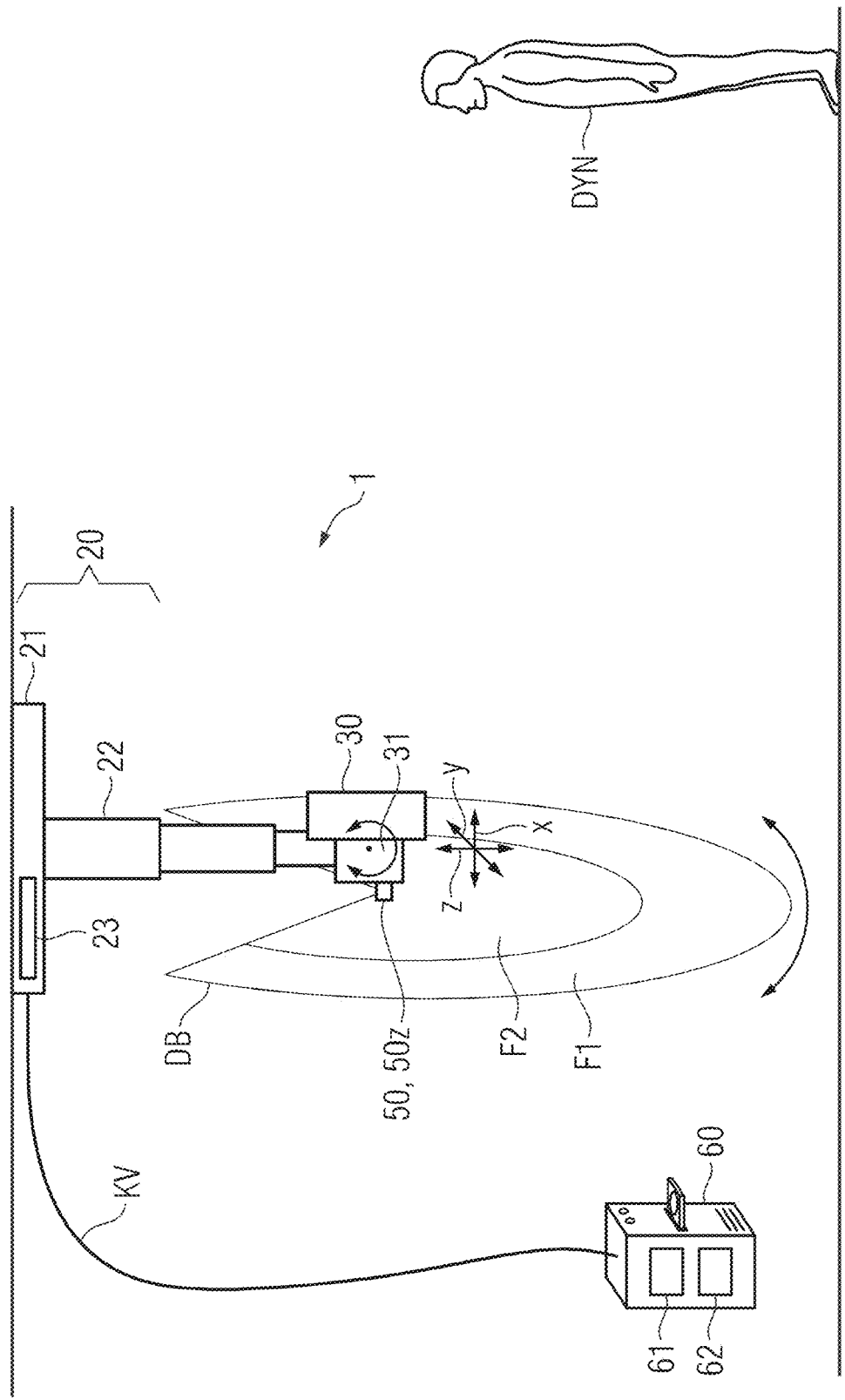

FIG. 2 shows an expanded view of the medical imaging system 1 according to an embodiment of the invention according to FIG. 1, wherein the expansion comprises a sensor unit 50 with a plurality of environmental sensors 50*x/y*, 50*z*. According to this embodiment (combination of FIG. 1 and FIG. 2) of the invention, it is proposed that an additional laser scanner 50*z* be attached to the X-ray tube 30 such that the detection range DB thereof spans a plane perpendicular to the horizontal plane, i.e. the further laser scanner 50*z* also scans the z direction and closely adjacent directions. In this respect, this embodiment of the invention enables spatial monitoring of the X-ray tube environment and in particular enables account to be taken of objects moving from below to above. In other words, here, the sensor unit is embodied for three-dimensional monitoring of the room.

In further embodiments, a single environmental sensor of the sensor unit 50 can also be embodied as a three-dimensional sensor.

For example, as shown in FIG. 2, only one laser scanner 50*z* can be provided while the room is nevertheless monitored in the x, y and z direction in that the laser scanner 50*z* together with the X-ray tube 30 is adjusted about a horizontal axis, for example the y-axis, during the scanning process. This also causes the detection range DB to be pivoted between a horizontal and a vertical (as shown here) alignment.

Alternatively, in order to achieve more flexible monitoring of the room, the laser scanner 50*z* can be arranged on the X-ray tube 30 or the telescopic arm such that it can be inclined about or oscillates about a horizontal axis independently of a tilting movement of the X-ray tube 30.

Figure 3:
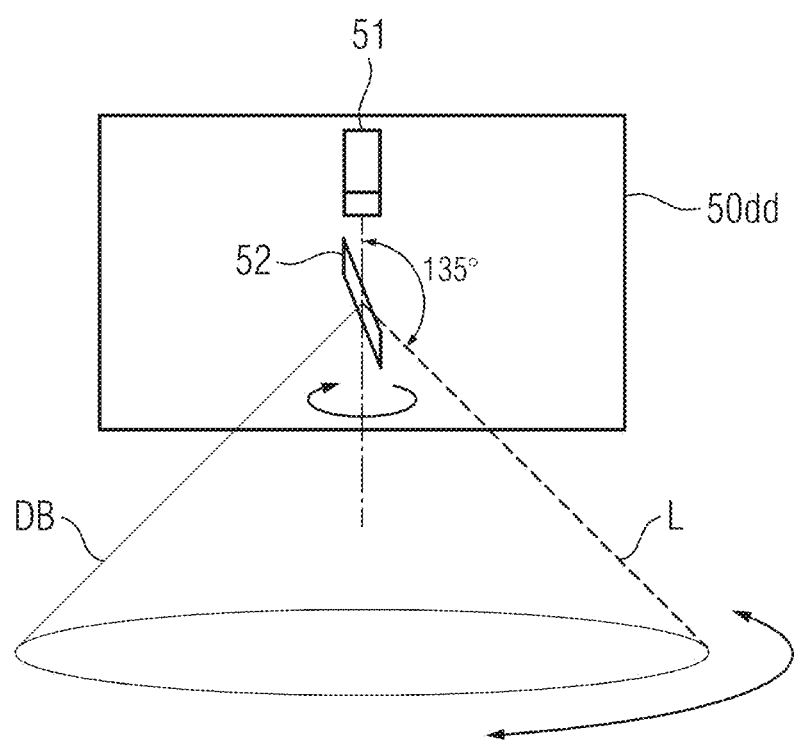

FIG. 3 shows a detailed view of a medical imaging system 1 according to the invention according to an alternative embodiment, likewise with a three-dimensional environmental sensor 50*dd*. Specifically, here an embodiment of an environmental sensor according to the invention is shown in the form of a laser scanner 50*dd*. For this purpose, the laser beam L generated by a laser beam source 51 is deflected by a mirror arrangement 52 not, as usual, at an angle of 90°, but at an angle deviating therefrom, for example 135°. Here, other angle settings are obviously possible. The mirror arrangement 52 is mounted rotatably so that the laser beam traverses the lateral surface of a cone during the scanning process, which corresponds to the detection range DB of this laser scanner 50*dd*. This likewise permits detection of dynamic obstacles in all three spatial directions.

Figure 4:
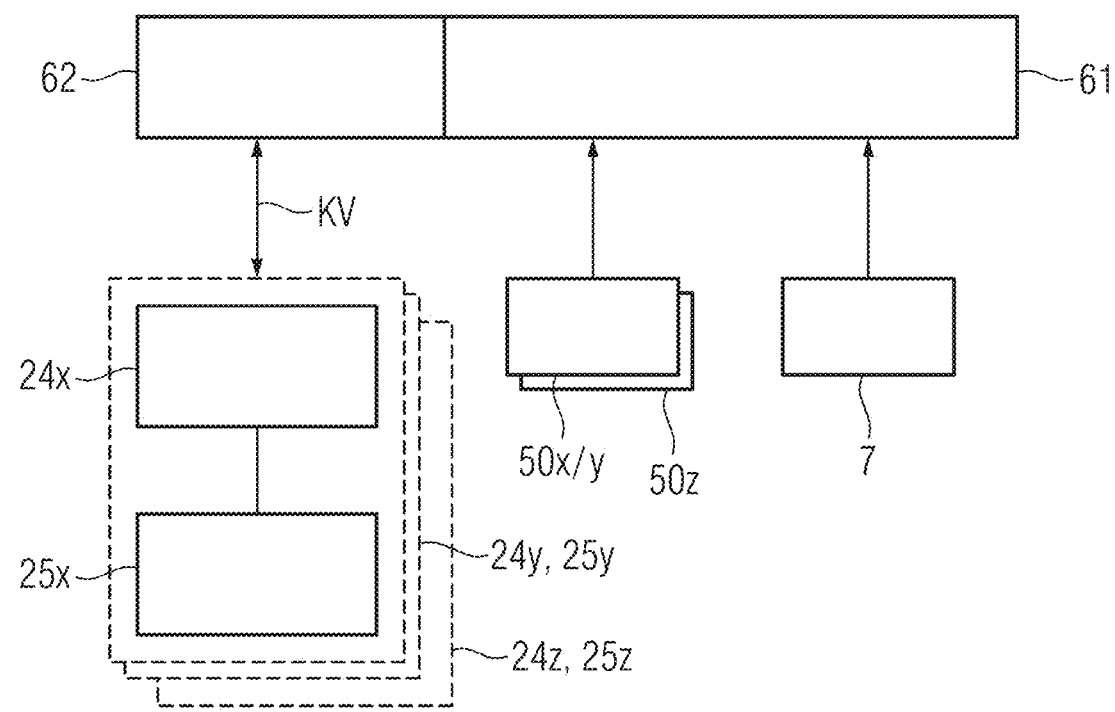

FIG. 4 shows a detailed view of a stand 20 according to an embodiment of the invention for a medical imaging system 1 according to a combination of FIGS. 1 and 2.

Environmental parameters acquired via laser scanners 50*x/y* and 50*z* are acquired via secure digital outputs of the laser scanner 50*x/y* and 50*z* and secure digital inputs at the interface 61 for the control unit 62. The drive regulator 24 can comprise a regulating unit for each degree of freedom, in particular the three spatial directions x, y, z. The drive module 25 can comprise a drive unit for each degree of freedom, in particular the three spatial directions x, y, z. If a violation of the warning field F1 of a laser scanner 50*x/y* or 50*z* is detected, i.e. a dynamic obstacle DYN is identified in the warning field F1, the drive regulator 24 and the drive module 25 of the drive unit 23 are controlled accordingly and the relevant drive regulators 24*x*, 24*y*, 24*z* of the drive unit 23 are induced via the communication link KV in the form of a field bus to monitor compliance with a reduced speed of movement for the drive modules 25*x*, 25*y*, 25*z* with the aid of the drive safety function SLS. This ensures that is only possible to approach objects, in particular dynamic obstacles DYN, at a reduced speed. If this speed threshold is exceeded, provision can be made to enforce an instantaneous halting of the adjustment movement via the drive safety function STO. If a further approach to the object results in a violation of the protective field F2 of one of the laser scanners 50*x/y* and 50*z*, likewise any movement is halted immediately. In some embodiments, the drive regulator 24 may still allow movement in the opposite direction via the drive safety function SDI and the drive module 25 can be controlled accordingly.

The tactile sensor 7 is also in contact with the interface 61 via a safe digital output so that, here too, if the sensor signal indicates a collision, the control unit 62 causes the movement of the drive regulator 24 and the drive module 25 to be halted via the drive safety function STO.

Figure 5:
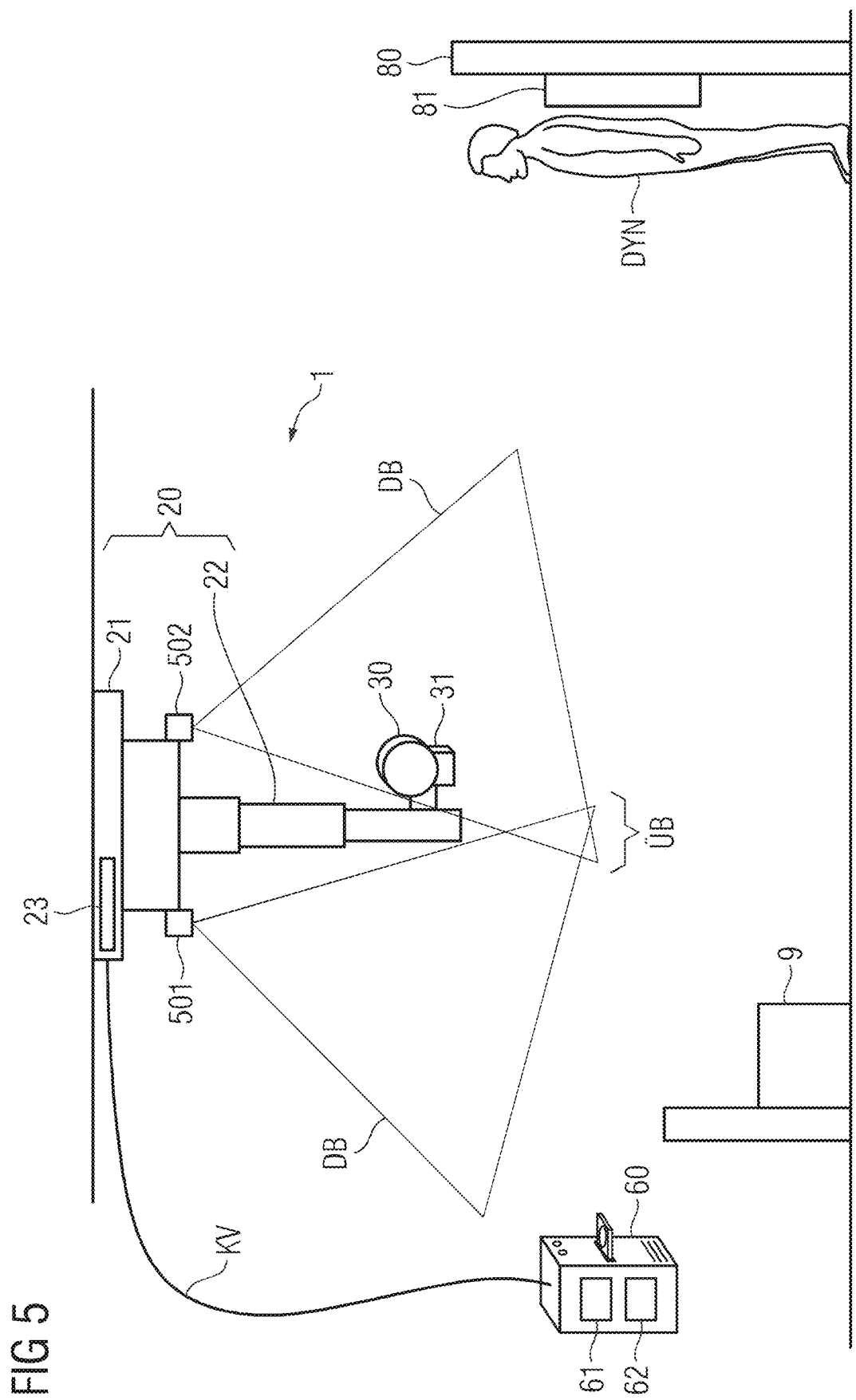

FIG. 5 shows a view of a medical imaging system in another embodiment. This embodiment differs from the form shown in FIGS. 1 and 2 as follows. Here, a plurality, i.e. at least two, environmental sensors 501 and 502 are provided in the sensor unit 50. The environmental sensors 501 and 502 are embodied as three-dimensional sensors in the form of depth sensors in the form of three-dimensional cameras. Both depth sensors 501 and 502 are arranged on a carriage of the stand 20 which is likewise embodied as a ceiling stand on which the telescopic arm 22 together with the X-ray tube 30 is also attached. Both environmental sensors are arranged with a vertically downward aligned detection field DB and specifically in such a way that at least the detection field DB of the environmental sensor 502 at least partially encloses the X-ray tube 30. This enables multiple advantages with respect to calibration, installation or error-analysis; a distance between environmental sensor and X-ray tube 30 can be derived directly from the environmental parameters. The detection ranges DB of the two environmental sensors 501 and 502 comprise an overlapping region ÜB, which can also be significantly larger than shown here. At least for this region, first-failure safety can be ensured during operation since both environmental sensors 501 and 502 monitor the region ÜB in redundant form and can replace each other in their function if necessary.

In this embodiment, the environmental sensors 501 and 502 in each case provide a distance profile across their detection ranges DB. The distance profile describes distances between the respective sensor and a mapped object, such as, for example, a rigid or fixed object such as a bucky wall stand 80 or a patient table 9 or dynamic obstacles such as a person DYN or the X-ray detector 81 arranged adjustably on the bucky wall stand.

Figure 6:
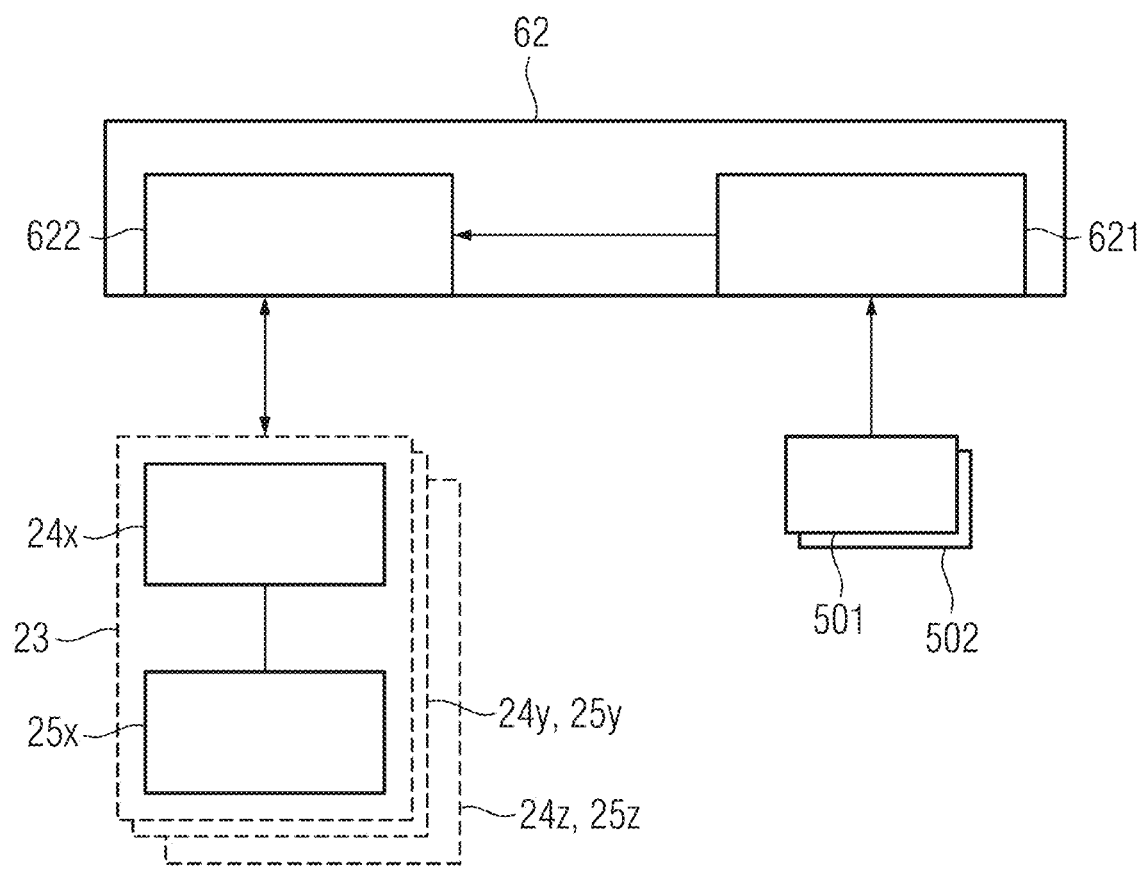

FIG. 6 shows a detailed view of a stand 20 according to an embodiment of the invention for a medical imaging system 1 according to FIG. 5.

Environmental parameters acquired via three-dimensional cameras 501 and 502 are acquired via the interface 61 (not shown here) for the control unit 62. Here, the control unit 62 comprises a sensor data processing unit 621 which in each case calculates a two-dimensional height map for each environmental sensor 501, 502 from the distance profiles. The height maps are supplied to the positioning unit 622 of the control unit 62 which, based thereon, generates control signals for the drive unit 23 comprising the drive regulator 24 and the drive module 25. Here too, the drive regulator 24 can comprise a regulating unit for each degree of freedom, in particular the three spatial directions x, y, z. The drive module 25 can comprise a drive unit for each degree of freedom, in particular the three spatial directions x, y, z. Here too, the safety functions SLS, STO and/or SDI can be implemented, but here based on height value thresholds and/or speed values.

Furthermore, in this embodiment camera-based patient positioning can take place since the patient's position and/or location can be identified by the camera system 501, 502 without active intervention by an operator provided the patient is located in one of the detection ranges. Activation and/or control of an adjustment movement of the medical imaging system by an operator's gestures or speech is also enabled without additional material expenditure.

Figure 7:
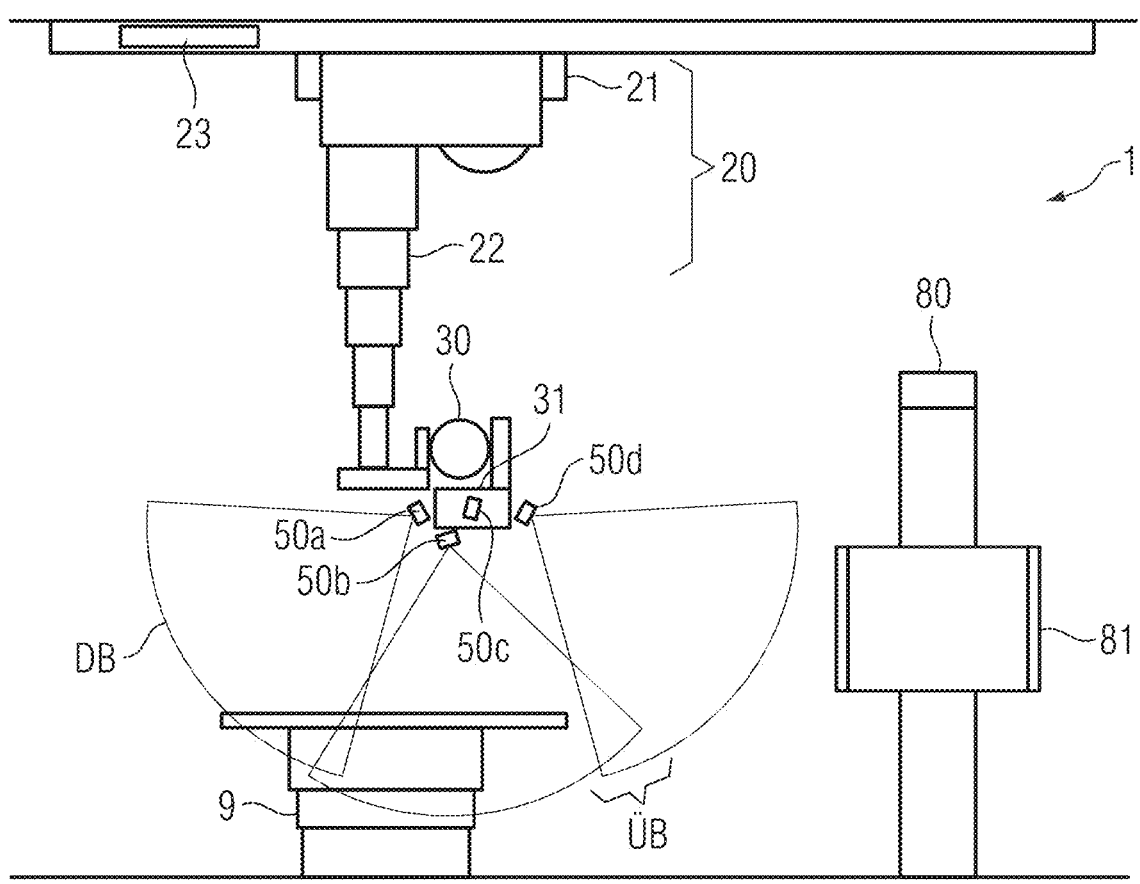

FIG. 7 shows a view of a medical imaging system in a further embodiment. This embodiment is characterized by a sensor unit 50 with a plurality of environmental sensors 50*a*, 50*b*, 50*c*, 50*d*, which are arranged such that their detection ranges DB form an envelope curve around the X-ray tube 30. The envelope curve is formed by the entirety of all detection ranges DB of the environmental sensors 50*a*, 50*b*, 50*c*, 50*d* and preferably forms a completely enclosed hemisphere that is aligned toward the floor. Here too, overlapping regions ÜB are embodied that allow first-failure safety during the operation of the ceiling stand.

In this embodiment, the environmental sensors 50*a*, 50*b*, 50*c*, 50*d* are formed as multi-technology radar sensors (for example via PCR—pulsed coherent radar). The combination of different radar technologies on one chip enables spatial and speed resolution in the mm range. In this embodiment, the environmental sensors 50*a*, 50*b*, 50*c*, 50*d* are integrated in the collimator 31 of the X-ray tube 30 and are hence embodied to acquire the direct environment of the X-ray tube 30. For a complete envelope curve around the X-ray tube 30, a plurality of environmental sensors including chips must be provided, preferably also more than the four environmental sensors 50*a*, 50*b*, 50*c*, 50*d* shown here. In this case, synchronization of the environmental sensors is possible so that an intersection of the detection ranges DB, here in the form of 'cones of view', during active radar scanning usefully intersect. Also, more than four environmental sensors are advantageous for realizing first-failure safety in order to enlarge the overlapping regions ÜB.

In order to achieve first-failure safety over the entire detection range of the sensor unit 50, which is typically required in medical applications, the environmental sensors' sensing mechanism, can, for example, be mounted on the carrier board in redundant form. Thus, for the size of a dynamic obstacle DYN (for example a person or an infusion stand, etc.), a completely redundant enclosed envelope curve is obtained around the moving X-ray tube 30 or stand 20. Moreover, suitable positioning of the environmental sensors 50*a*, 50*b*, 50*c*, 50*d* increases the functional radius and the possible applications. For example, a set tube-detector distance (SID, source-image-distance) can be checked for plausibility in order to achieve correct alignment with free recordings. Furthermore, this example embodiment is suitable for tracking the format of the collimator opening during movement. In this embodiment, the material costs are advantageously low.

The sensor unit 50 can also be used as a further reference system for ascertaining/monitoring the position of the device in the treatment room. Thus, for example, the position of the ceiling stand 20 in the room can be verified and hence be available as a control/protection path of the system architecture/computing unit 60 of the medical imaging system 1.

Figure 8:
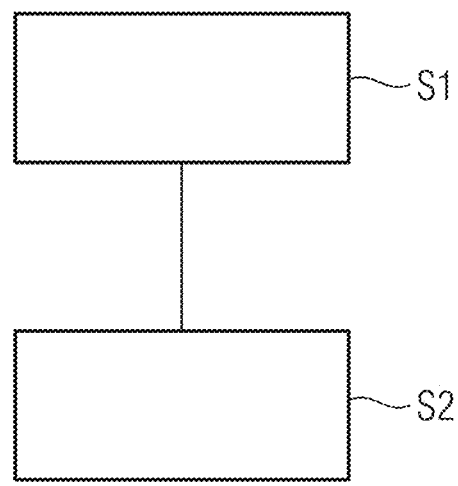

FIG. 8 shows a method according to an embodiment of the invention for controlling a stand 20 according to an embodiment of the invention. The method can, for example, be carried out with a stand according to FIGS. 1 to 7 or different stands. The method comprises a plurality of steps.

In a first step S1, at least one spatial environmental parameter is acquired via the sensor unit 50.

In a second step S2, an adjustment movement of an X-ray tube 30 is controlled via the control unit 62, wherein the controlling comprises generating control signals for a drive unit 23 and adapting these based on the at least one environmental parameter.

In one optional embodiment of the invention, step S1 can comprise acquiring a depth image. In this embodiment, step S2 can comprise ascertaining a cell-based two-dimensional height map from the depth image. In other words, the distance values of an acquired spatially encoded distance profile are transferred into a height map, wherein the cell-based height values are related to a background, for example an examination room, in which the medical imaging system 1 is located.

In another optional embodiment of the invention, step S1 can also comprise acquiring a depth image. In this embodiment, step S2 can comprise ascertaining a multi-level surface map from the depth image, which is then used as the basis for controlling the path planning for the ceiling stand.

In a further optional embodiment, step S2 comprises using the at least one acquired environmental parameter to identify at least one dynamic obstacle DYN moving in the immediate vicinity of the X-ray tube 30. For this purpose, it can also be provided that an environmental parameter is acquired in the form of a speed of movement for the dynamic obstacle DYN.

In a further optional embodiment of the method according to the invention, step S2 comprises determining a trajectory, speed of movement, direction of movement and/or halting of movement for the X-ray tube 30 that is adapted to the identified dynamic obstacle DYN. For example, the above-described drive safety functions can be used for this purpose.

Where not explicitly done, but useful and within the spirit of the invention, individual example embodiments, individual partial aspects or features thereof may be combined or interchanged without departing from the scope of the present invention. Where transferable, advantages of the invention described with reference to one example embodiment of the invention also relate to other example embodiments without being explicitly mentioned.

Although the invention has been illustrated and described in detail by the preferred embodiments, the invention is not limited by the disclosed examples and other variations can be derived herefrom by the person skilled in the art without departing from the scope of protection of the invention.

Even if not explicitly stated, individual example embodiments, or individual sub-aspects or features of these example embodiments, can be combined with, or substituted for, one other, if this is practical and within the meaning of the invention, without departing from the present invention. Without being stated explicitly, advantages of the invention that are described with reference to one example embodiment also apply to other example embodiments, where transferable.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A stand for a medical imaging system, comprising:
   an X-ray tube; and
   a driver configured adjust the X-ray tube in at least two spatial degrees of freedom;
   at least one environmental sensor configured to acquire at least one environmental parameter; and
   a controller configured to
      control an adjustment movement of the X-ray tube by generating control signals for the driver, and
      adapt the adjustment movement based on the at least one environmental parameter,
   wherein the X-ray tube is in a detection field of the at least one environmental sensor.

2. The stand of claim 1, wherein the at least one environmental sensor includes a plurality of environmental sensors.

3. The stand of claim 2, wherein detection fields of at least two of the plurality of environmental sensors at least partially overlap.

4. The stand of claim 3, wherein
   detection ranges of the at least two of the environmental sensors form an envelope curve around the X-ray tube.

5. The stand of claim 2, wherein at least one of the plurality of environmental sensors is a three-dimensional sensor.

6. The stand of claim 2, wherein the at least one environmental parameter includes at least one of a distance or a distance profile.

7. The stand of claim 2, wherein the plurality of environmental sensors are on a carriage of the stand with a vertically downward aligned detection field.

8. The stand of claim 2, wherein the plurality of environmental sensors are on the X-ray tube with a horizontally aligned detection field.

9. The stand of claim 2, wherein
   the plurality of environmental sensors are configured to acquire a depth image, and
   the controller is configured to ascertain a cell-based two-dimensional height map based on the depth image.

10. The stand of claim 2, wherein
the plurality of environmental sensors are configured to acquire a depth image, and
the controller is configured to ascertain a multi-level surface map based on the depth image.

11. The stand of claim 1, wherein the at least one environmental sensor is a three-dimensional sensor.

12. The stand of claim 1, wherein the at least one environmental parameter includes at least one of a distance or a distance profile.

13. The stand of claim 1, wherein the at least one environmental sensor is on a carriage of the stand with a vertically downward aligned detection field.

14. The stand of claim 1, wherein the at least one environmental sensor is on the X-ray tube with a horizontally aligned detection field.

15. A medical imaging system comprising the stand of claim 1.

16. The stand of claim 1, wherein
the at least one environmental sensor is configured to acquire a depth image, and
the controller is configure to ascertain a cell-based two-dimensional height map based on the depth image.

17. The stand of claim 1, wherein
the at least one environmental sensor is configured to acquire a depth image, and
the controller is configured to ascertain a multi-level surface map based on the depth image.

18. A method for controlling a stand for a medical imaging system, the stand including an X-ray tube, a driver configured to adjust the X-ray tube, at least one environmental sensor, and a controller, the method comprising:
acquiring at least one spatial environmental parameter via the at least one environmental sensor; and
controlling an adjustment movement of the X-ray tube via the controller, the controlling including generating control signals for the driver and adapting the control signal based on the at least one spatial environmental parameter, and
wherein the X-ray tube is in a detection field of the at least one environmental sensor.

19. The method of claim 18, wherein
the acquiring the at least one spatial environmental parameter includes acquiring a depth image, and
the controlling includes ascertaining a cell-based two-dimensional height map based on the depth image.

20. The method of claim 18, wherein
the acquiring the at least one spatial environmental parameter includes acquiring a depth image, and
the controlling includes ascertaining a multi-level surface map based on the depth image.

21. The method of claim 18, wherein the controlling includes identifying at least one dynamic obstacle based upon the at least one spatial environmental parameter.

22. The method of claim 21, wherein the controlling includes determining at least one of a trajectory, speed of movement, direction of movement or halting of movement for the X-ray tube that is adapted to the identified dynamic obstacle.

* * * * *